United States Patent
Mistrik (10) Patent No.: US 7,197,402 B2
(45) Date of Patent: Mar. 27, 2007

(54) DETERMINATION OF MOLECULAR STRUCTURES USING TANDEM MASS SPECTROMETRY

(75) Inventor: Robert Mistrik, Bratislava (SK)

(73) Assignee: Highchem, Ltd., Bartislava (SK)

( * ) Notice: Subject to any disclaimer, the term of this patent is extended or adjusted under 35 U.S.C. 154(b) by 27 days.

(21) Appl. No.: 10/967,018

(22) Filed: Oct. 14, 2004

(65) Prior Publication Data

US 2006/0085142 A1    Apr. 20, 2006

(51) Int. Cl.
*G01N 31/00* (2006.01)
*G06F 19/00* (2006.01)

(52) U.S. Cl. .......................... 702/27; 702/22

(58) Field of Classification Search ................ 702/22, 702/27, 30, 186; 250/281, 282, 292; 435/6, 435/7.1
See application file for complete search history.

(56) References Cited

U.S. PATENT DOCUMENTS

| | | | |
|---|---|---|---|
| 5,072,115 A | 12/1991 | Zhou | 250/281 |
| 5,453,613 A | 9/1995 | Gray et al. | 250/281 |
| 6,362,473 B1 | 3/2002 | Germanus | 250/282 |
| 6,455,321 B1 | 9/2002 | Chace | 436/173 |
| 6,623,935 B2 | 9/2003 | Overney et al. | 435/7.1 |
| 6,624,408 B1 | 9/2003 | Franzen | 250/282 |
| 6,674,069 B1 | 1/2004 | Martin et al. | 250/287 |
| 6,675,104 B2 | 1/2004 | Paulse et al. | 702/22 |
| 2002/0063206 A1* | 5/2002 | Bateman et al. | 250/281 |
| 2003/0236636 A1 | 12/2003 | Yoshinari et al. | 702/27 |
| 2004/0229369 A1 | 11/2004 | Kruappa et al. | 436/86 |
| 2004/0245461 A1* | 12/2004 | Senko | 250/292 |

FOREIGN PATENT DOCUMENTS

WO    WO 02/48699    12/2001

OTHER PUBLICATIONS

Gaucher et al., "STAT, A Saccharide Topology Analysis Tool Used in Combination with Tandem Mass Spectrometry", Anal. Chem., vol. 72, pp. 2331-2336, (2000).

* cited by examiner

*Primary Examiner*—Bryan Bui
(74) *Attorney, Agent, or Firm*—Weingarten, Schurgin, Gagnebin & Lebovici LLP (57) ABSTRACT

Methods for determining the chemical structures, substructures and/or ionic structural arrangements of unknown or partially structurally characterized compounds from mass spectrometric data are disclosed. The methods of the invention are directed to elucidating the molecular structures of compounds by identifying the structures of ions generated from those compounds through the use of tandem mass spectrometry and subsequently conducting a library search of structurally characterized tandem product spectra from known ions for specific matches. The collective structural information and/or alternative structural candidates are then constructed from the determined ion structures and other structural characteristics using a structure generator and/or a structure assembly and/or a structure reduction system. The structure or substructure determination process can be continuously improved by adding additional data, e.g., information obtained from molecules previously structurally characterized using this method.

15 Claims, 3 Drawing Sheets

DETERMINATION OF MOLECULAR STRUCTURES USING TANDEM MASS SPECTROMETRY

CROSS REFERENCE TO RELATED APPLICATIONS

N/A

STATEMENT REGARDING FEDERALLY SPONSORED RESEARCH

N/A

BACKGROUND OF THE INVENTION

Determining the structure of unknown compounds is of prime importance to practioners of analytical chemistry. In particular, mass spectrometry has been and continues to be a widely employed structure characterization technique in the chemical, biological and medical sciences. The chemical structure of interest can range from very simple diatomic arrangements to very complex protein or DNA macromolecules. Considerable effort has been invested into hardware and software systems capable of efficient structure determination of unknown compounds by means of mass spectrometry.

Widely used library search systems are designed to identify compounds represented in the reference library that might have generated the submitted single stage or tandem mass spectrometry spectra from the unknown compound. These systems are based on an assumption that a chemical entity exhibits a unique spectral fingerprint that should have a counterpart in a reference library (McLafferty and Stauffer 1985; Stein and Scot 1994; Sander 1999; Gross et al. 2002; Alfassi 2003). When the unknown compound is not represented in the library, the compound cannot be identified by this means. To overcome this shortcoming, various "interpretative" library search techniques have been developed to derive at least partial structural information by estimating the probability of substructure occurrence and absence in a single stage mass spectrum using a predefined set of substructures (Damen et al. 1978; Warr 1993; Stein 1994). The identification of a substructure from a given mass spectrum using such a method can be difficult or even impossible because its success will depend on the relative rates of competitive processes that depend, in turn, on other structural features of the molecule. Even for substructures that commonly produce characteristic patterns, the actual "signatures" can be highly variable (Stein 1994).

Statistical pattern recognition methods have been applied for the selective detection of compound classes or individual functional groups from mass spectra. Most of these methods are based on the presumption that common structural moieties exhibit identical or similar fragmentation patterns (Scsibrany and Varmuza 1992; Drablos 1992; Lohninger 1994; Lebedev and Cabrol-Bass 1998; Klagkou 2003). To achieve statistically relevant results, a relatively large number of suitable spectra of compounds with common structural properties must be processed. Multivariate statistical methods have been successfully employed in the determination of certain structural features in selected data sets, usually in the range of 70–90% correct identifications; however, erroneous classification cannot be avoided. Since the mass spectrum reflects not only the relative rates of competitive processes but also complex gaseous ion thermochemistry, the dynamics of the reaction are highly variable. Even structurally highly similar compounds often do not exhibit a uniform fragmentation pattern. As a consequence, multivariate statistics and related methods cannot alone be considered as general purpose and reliable interpretation approachs.

Various methods for the interpretation of mass spectra based on expert systems or artificial intelligence have been developed (Lindsay et al. 1980; Warr 1993 Part 2). These methods employ a variety of advanced mathematical algorithms to derive structural information from spectra using individual or a combination of pattern recognition methods, decision trees, empirical rule-based systems, knowledge bases, exploratory techniques and other heuristic systems. A central problem when dealing with expert systems and artificial intelligence methods is their narrow application range in terms of structural variety. These methods need to be selectively trained for each chemical class of interest. In order to perform satisfactorily, these methods require, in the training phase, a statistically relevant number of spectral representatives for each structural class or group, which may pose a serious problem if no such spectra are available. On the other hand, specific applications that do not require universal substructure determination capabilities can benefit from the inherent selectivity of these methods, which allows the achievement of high probabilities of correct identification.

In the past, there have been several attempts to design algorithms for structure elucidation based on substructure identification from tandem mass spectra (Enke et al. 1987; Wade et al. 1988; Palmer et al. 1989). Although these systems include some expert system features, they are very similar to the interpretative techniques of single stage library search methods mentioned above. These method try to derive substructural information from a comparison of calculated m/z value ratios and/or neutral loses of predefined single- or diatomic substructures stored in a library with correspondingly calculated parameters from analyzed tandem spectra. Owing to the immense structural variability and the huge number of structurally different isobaric ions, the m/z ratios and neutral lose values, even with exact mass precision, are usually not distinct enough to provide rules for unambiguous identification of the predefined fragment structures because of the immense combinatorial cardinality of structures or fragments with identical molecular mass.

With the advent of proteomic research, a full variety of new structure characterization techniques for linear molecules has emerged. One method compares an experimental product mass spectrum with theoretical spectra calculated from amino acid sequences of database proteins and identifies the sequence that best fits the tandem mass spectrum (Yates III et al. 1995; Perkins et al. 1999; Sadygov et al. 2002; Anderson et al. 2003). An alternative approach, termed "de novo sequencing," converts the fragment ion mass values derived from spectra into a ranked list of most probable amino acid sequences (Shevchenko et al. 1997; Fernandez-de-Cossio et al. 1998; Dancik et al. 1999; Horn et al. 2000). The major limitation of these methods is the fragmentation model which considers that peptides fragment in a uniform manner. A considerable number of routinely observed peptide spectra do not exhibit a contiguous series of backbone cleavage sequence ions because of the vast variability of dissociations patterns. This becomes even more prevalent in non-linear molecules, preventing the adoption of proteomic methods for the interpretation of a majority of organic compounds.

There has been a rapid expansion in the use of tandem mass spectrometry for the structural elucidation of organic compounds. In tandem mass spectrometry, the ions that emerge from the ionization process (precursor ions) can be further isolated and fragmented by means of collision induced dissociation or various other ion activation techniques that give rise to second stage spectra called product spectra. Given the appropriate hardware, the isolation and activation procedures can be successively repeated in several stages. Resulting product spectra exhibit fragmentation peaks from isolated ions, providing an added dimension to the overall fragmentation pattern. Although tandem mass spectra along with the masses of their precursor ions contain important portions of structural information of the elucidated molecule, the structural arrangement remains ciphered through the set of product fragment masses. Accurate mass measurements can greatly reduce the number of possible elemental compositions for a given fragment mass. Still, the immense variability of dissociation patterns obscures structural determination.

With the introduction of atmospheric pressure ionization techniques in combination with tandem mass spectrometry to analytical chemistry, library techniques for tandem spectra have been developed (Dheandhanoo 1988; Martinez and Ganguli 1989; Martinez 1991; Bristow et al. 2004; Joseph and Sanders 2004; Pittenauer et al. 2004). There are, however, several potential difficulties of obtaining standard library searchable spectra. As different types of analyzers favor different fragmentation pathways for the same compound due to different kinetic energies of the precursors, different collision energy regimes, few or multiple collisions and unimolecular or consecutive decays, data from different types of analyzers cannot be easily incorporated in one database. Although, despite the inherent variability of sample preparation, experimental conditions and instrumentation designs, attempts have been made to create libraries applicable to a wide range of possible "real-life" situations and to automate the structure identification process, improved systems still are needed (Sander 1999; Mistrik et al. 2003; U.S. Pat. Nos. 6,624,408, 6,623,935, 5,072,115, 4,008,388).

BRIEF SUMMARY OF THE INVENTION

The methods of the invention are directed to elucidating the molecular structures of completely unknown or partially structurally characterized compounds by identifying the structures of ions generated from those unknowns through the use of tandem mass spectrometry and (multiple-stage mass spectrometry) and subsequently conducting a library search of tandem product-ion spectra (product-ion spectra) of structurally known precursor ions for specific matches. The collective structural information and/or alternative structural candidates are then constructed from the determined ion structures and/or other structural characteristics using a structure generator and/or a structure assembly and/or a structure reduction system. The structure or substructure determination process can be continuously improved by adding additional data, e.g., information obtained from molecules previously structurally characterized using this method.

Specifically, the invention provides an effective method for interpretation of mass spectral data and allows the generation of a single or a limited set of possible structures or substructure proposals for the analyzed molecule. The method of the invention uses a library of structurally characterized product-ion spectra acquired by tandem mass spectrometry to derive the molecular structure of the unknown or partially structurally defined molecule to be analyzed. Given the analogous spectral fingerprints of structurally equivalent fragment ions, the individual pieces of structural information (fragment structures) can be obtained by a search of analogous product-ion spectra from various tandem stages of previously analyzed, known molecules contained in a library of structurally characterized product-ion spectra. Once the search results are obtained, the identified fragment structures can be translated into substructures of the analyzed molecule and listed, and/or the overall structural arrangement of the analyzed molecule can be reconstructed in a structure generator using the obtained substructural information, and/or supplementary information such as the exact molecular mass, molecular formula, a priori known functional groups, isotopic pattern, mass defect, nitrogen rule, rings plus double-bonds, neutral losses, and/or physico-chemical properties of the analyzed structure.

BRIEF DESCRIPTION OF THE SEVERAL VIEWS OF THE DRAWINGS

Other features and advantages of the invention will be apparent from the following description of the preferred embodiments thereof and from the claims, taken in conjunction with the accompanying drawings, in which:

DETAILED DESCRIPTION OF THE INVENTION

As implied by quasi-equilibrium theory, the probabilities of the various possible decomposition product-ions of an ion depend only on its structure and internal energy and not on the method used for the ionization, or on the structure of the precursor for, or formation mechanism of, the ion undergoing decomposition (McLafferty and Turecek, 1993). Thus, the spectra resulting from the isolation, activation and subsequent dissociation of structurally equivalent ions exhibit analogous fragmentation patterns, predominantly independent of tandem stage. The degree of spectral analogy between the product-ions of two structurally equivalent ions undergoing decomposition is dependent on the differences in sample preparation and experimental conditions. Analogous spectra can be defined as two spectra that closely reflect the correspondence of m/z values and their relative intensity ratios in observed spectral peaks. The spectral analogy is usually quantitatively expressed as a single value termed the match factor. The threshold value of the match factor for positive identification can be set individually. If the spectral acquisition process follows a standardized experimental protocol, highly reproducible, transferable and library searchable tandem product-ion spectra can be acquired (Bristow et el. 2004; Pittenauer et al. 2004).

If the standardized criteria cannot be met completely or if differences in internal energies are expected, several product-ion spectra for the same precursor ion can be acquired using various sample preparation processes (pH, solvent, buffer, salt content etc.) and experimental condition options (instrument design, ionization energies, activation energies, collision energies, collision gas, collision gas pressure, isolation width, accumulation cut-off, fragmentation amplitude, chromatographic system, etc.) to cover a number of possible variations in spectra appearances. In addition, various mathematical methods can be used to harness the spectral dissimilarities and allow correct identification of fragment structures. One example of such a method consists of obtaining parameter matching values that are calculated by weighting each acquisition parameter for its effect on a mass spectrum. Parameter matching values are then used for the calculation of a match factor, which is used for compound identification (Sander 1999)

Figure 1:
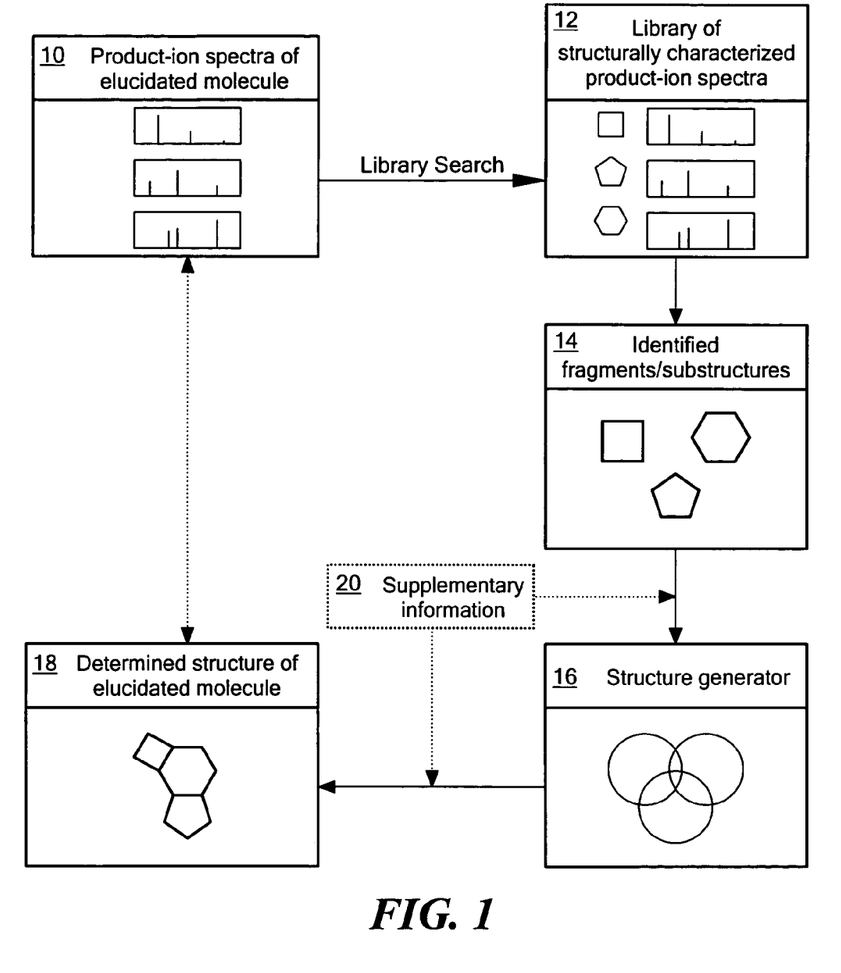
FIG. 1 is a schematic view of the method for the determination of molecular structures using tandem mass spectrometry in accordance with the present invention.

It is the idea of this invention to identify structures of ions generated by mass spectrometry by searching analogous product-ion spectra of precursor ions of analyzed molecules in a library of product-ion spectra with previously determined structures of precursor ions (a library of structurally characterized product-ion spectra). FIG. 1 is a schematic view of the method of the present invention. As shown in FIG. 1, tandem product-ion spectra 10 and/or mass spectra of an elucidated molecule are acquired and searched against a library of structurally characterized product-ion spectra 12. Fragment structures 14 associated with retrieved library product-ion spectra indicate the presence of identical or structurally equivalent fragment structures in the elucidated molecule. Identified fragment structures and/or substructures can be listed or processed by a structure generator 16 that reconstructs the structural arrangement of the elucidated molecule 18 using optional supplementary molecular information 20. The determined structure or structures or substructure or substructures are assumed to correspond to the elucidated molecule.

Prior to or during the determination of molecular structure, a library of structurally characterized product-ion spectra must be established. Product spectra can be acquired from any compound of known structure existing as a pure substance or present in a well defined mixture. The compound of known structure can be a molecule with an exactly definable chemical structure with a finite number of atoms, or it can be a polymer structure with a variable or unknown number of atoms with a fully or partially known atomic arrangement. Product spectra can be acquired using various ionization, ion separation or activation mass spectrometric techniques. Product spectra can be acquired from various tandem stages (MS.sup.n). MS.sup.n is a technique where ion formation/fragmentation and subsequent decomposition of the original ions is carried out "in tandem" and n>1. Using multiple m/z analyzers and an ion beam results in "tandem in space" (e.g. triple-quadrupole and quadrupole-TOF mass spectrometers). Using ion-trap mass spectrometers (quadrupole or magnetic) results in "tandem in time" (Sparkman 2000).

A structurally characterized product-ion spectrum should contain the molecular mass and/or m/z value of the precursor ion, a list of m/z values along with relative and/or absolute intensities of product-ion ions, ion polarity, charge state, the structure of the precursor ion and/or the structure of the primary (parent) molecule. The isolation width used to isolate the precursor ion is optional; however, this information can enhance the reliability of correct fragment identification. Product-ion spectra are acquired by isolation, activation and subsequent decomposition of single or multiple, positively or negatively charged ions arising from ionization, decomposition, dimerization, charge buildup, adduct or cluster formation processes.

For the purpose of library creation, precursor ions (isolated, activated and dissociated ions) can be selected using various criteria, but, generally, the more product-ion spectra that are generated, the more comprehensive a library can be built. However, product-ion spectra that exhibit large chemical, electronic or other noise or low to moderate signal to noise ratios should be considered for inclusion into the library only after manual or automatic examination and/or employing noise reduction or compensation methods. There are several mathematical or experimental methods available for extracting useful spectral information from noisy signals that can be applied. Since the reference compound used for creation of a library of product-ion spectra is usually available in sufficient amount in pure form or is present in a well-characterized mixture, a number of repeated acquisitions of product-ion spectra are possible using various sample preparation and experimental options. This allows also acquisition of replicate product-ion spectra (scans) of identical precursor ions and identical settings so as to compute average, composite autocorrelation or other transformed spectra to obtain representative spectra with reduced artifact or random fluctuations. When a reference library of structurally characterized product-ion spectra is created for the purpose of carrying out the method of this invention, the sample preparation and experimental conditions should be consistent with conditions expected in the spectra acquisition process of the molecule whose structure is to be elucidated, or single or multiple mathematical methods should be applied to harness the inconsistency. The structure of the precursor ion (fragment structure) can be obtained by various means: manually proposed by a mass spectrometrist, automatically proposed by fragmentation prediction algorithms using general fragmentation rules (Mistrik, 2001) and/or a fragmentation library (Mistrik, 2004) and/or by comparative analysis of structural patterns of molecules exhibiting single or multiple comparable product-ion spectra and/or by using any procedure able to assign fragment structure to a precursor ion.

The product-ion spectra acquisition can be accomplished using low or high resolution and/or accuracy mass spectrometric equipment. High resolution is often inherently accompanied with high accuracy, and single term "high resolution" is a synonym for both capabilities. For the purpose of this invention, low or high resolution product-ion spectra or their combination can be used. For the assignment of fragment structure to a precursor ion, in the process of creating structurally characterized product-ion spectra, it is extremely beneficial to have high resolution spectra since the accurate m/z values of precursor and product-ion ions greatly reduce the number of possible molecular formulas for fragment structures. Also, the determination of the structural arrangement for the elucidated molecule can profit from exact mass measurements by constraining the elemental composition of the elucidated molecule and by consistently checking between the calculated mass of recognized fragment structures and accurate m/z values of precursor and product-ion ions. However, the high resolution spectra are not necessary for the methods of this invention, and low resolution spectra can be used as well. Also, the combination of low and high resolution spectra in library creation and structure determination is possible.

Once a structurally characterized product-ion spectrum with optional complementary data has been obtained, it can be stored in a database and/or computer program or any appropriate readable form to provide access to the information at any desirable time. Since the individual pieces of the stored information for a single record may be accessed at different times, the corresponding data can be independently compartmentalized. It is preferred that such data collection and database manipulation be achieved through the use of a digital computer. An exemplary database has been created using appropriate database technology. The library of structurally characterized product-ion spectra serves as a knowledge base for determining the structural or substructural arrangement of the elucidated molecule, as described further below.

To start the determination of the structural or substructural arrangement of the elucidated molecule, product-ion spectra of various tandem stages ($MS^n$; n>1) of the molecule are acquired. The elucidated molecule can be a molecule with an exactly definable chemical structure with a finite number of atoms or it can be a polymer structure with a finite or variable number of atoms. The selection of precursor ions and tandem stage can be accomplished automatically by the mass spectrometer or manually by an operator and can be performed before, or even interactively during, the structure determination process. The criterion for automated selection of precursor ions can be absolute or relative peak intensity; mass range; a predefined list of desired or disallowed m/z values; expected pseudomolecular, multiply charged, cluster or adduct ion m/z values; and/or any appropriate algorithmic or database method for ion selection. If the product-ion spectra of second and higher stages ($MS^n$; n>1) are generated from multiple precursor peaks corresponding to the set isolation width, the m/z value of the precursor ion can be calculated from the overall decomposition pattern, or it can be determined according to already recognized fragment structures. If interactive precursor ion selection is intended, communication between processing software and mass spectrometric equipment would be required. This feature is also one point of the invention. The processing software can continuously perform a quick precursor ion m/z value search or a more time consuming full or partial spectra search in the library of structurally characterized product-ion spectra or in its subset, depending on the available time window and speed of the search, to determine if a sufficient number of generated product-ion spectra are potentially or in fact represented in the library. If not, the processing software can proceed with the selection of other available precursor ions of the elucidated molecule at various stages, if the signal to noise ratio, ion current and/or other parameters of precursor peaks are at acceptable levels. In addition to the wide ranging screening, the precursor ion selection process can also be directed to confirm or reject specific structural or substructural information in the elucidated molecule by selecting precursor ions that are related to the investigated structural/substructural information.

Figure 2:
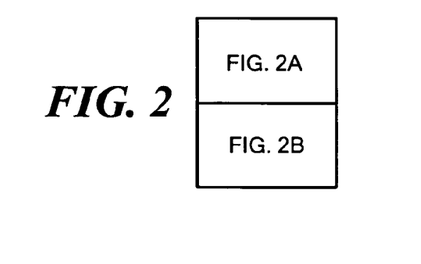
FIG. 2 depicts an example of the interpretation of product-ion spectra of Ampicillin utilizing the method of the present invention.
Figure 2A:
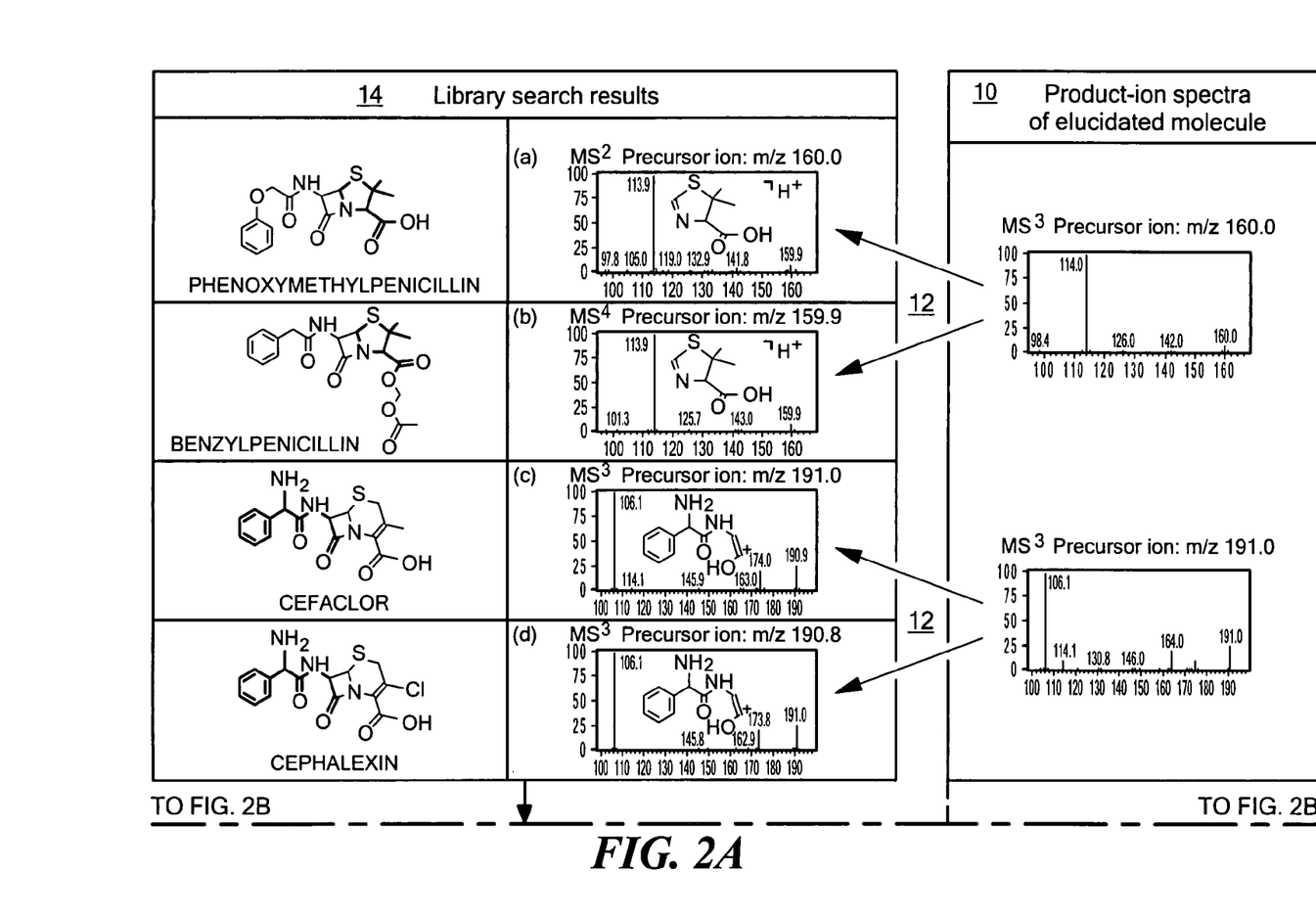
Figure 2B:
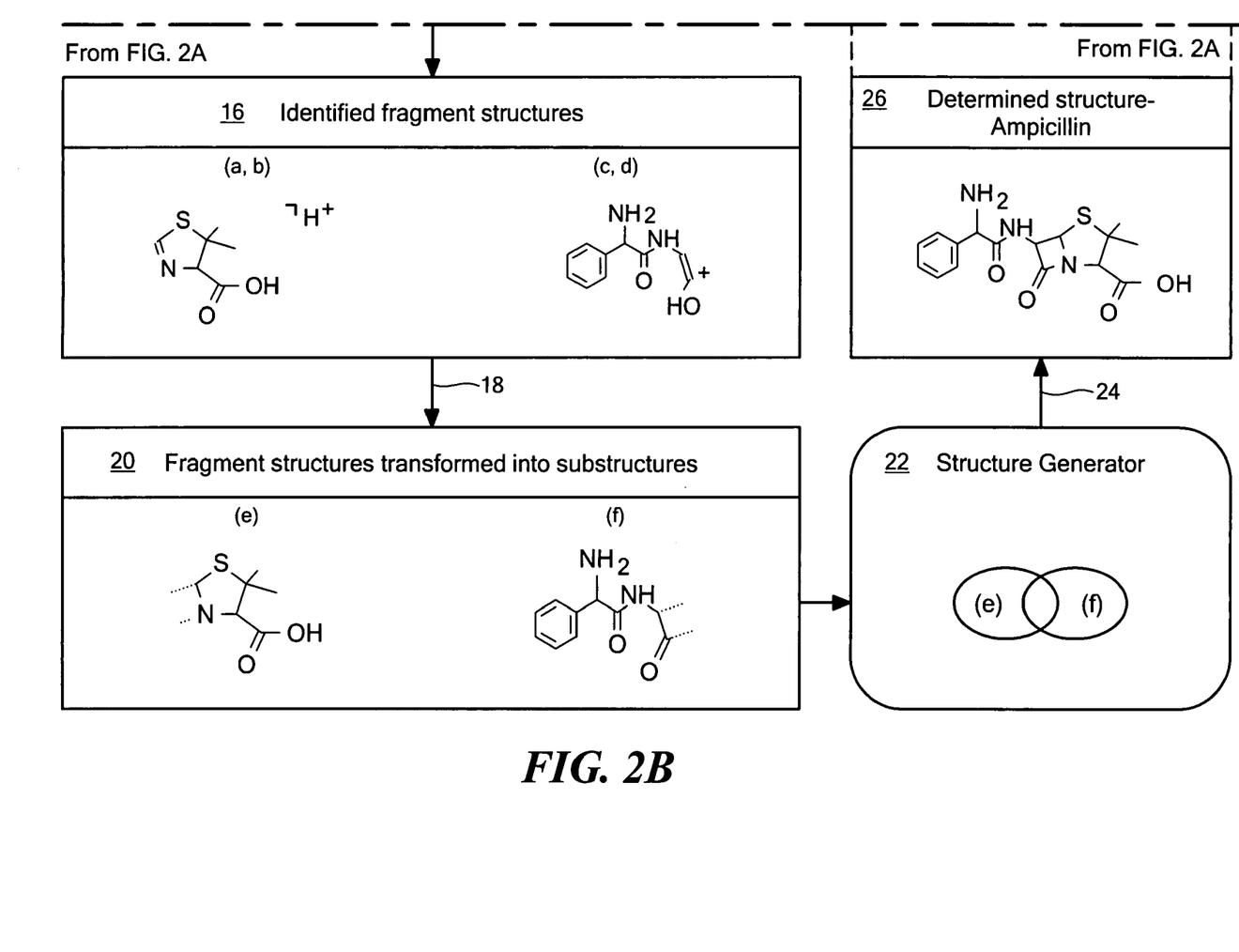

The methodology for the acquisition of library product-ion spectra, describe above, is applicable to the acquisition of product-ion spectra of elucidated molecules. Once the product-ion spectra of various tandem stages have been acquired and a compatible library of structurally characterized product-ion spectra is available, the spectra can be searched against the library. The library search process is based on a comparison of product-ion spectra of an elucidated molecule and spectrally characterized product-ion spectra in a library. Unlike other methods, in this invention the fragment structures are unambiguously determined by retrieving library product-ion spectra that are analogous to product-ion spectra of the elucidated molecule. As previously explained, tandem stage disparity is allowed so that, for example, $MS^2$ product-ion spectra can be compared with $MS^3$ spectra, as shown in FIG. 2. If the spectral comparison procedure reveals the required degree of analogy between a library product-ion spectrum and a product-ion spectrum of the elucidated molecule, the fragment structure assigned to the library product-ion spectrum is assumed to be identical or structurally equivalent with the precursor ion of the product-ion spectrum of the elucidated molecule. An identified fragment structure is added to a newly created list or to an existing list of previously identified fragment structures.

Various spectra comparison methods (spectra search algorithms) for single stage experiments have been developed in the past (McLafferty and Stauffer 1985; Stein and Scot, 1994; Sander, 1999; Gross et al., 2002; Alfassi, 2003). Those methods or their optimized derivitives can be utilized for purpose of this invention. In contrast to single stage spectra comparison methods, product-ion spectra offer a important additional characteristic parameter or parameters that can significantly contribute to correct fragment identification, and this is the mass or m/z value of the precursor ion and/or the isolation width. Prior to comparison of the spectra, these parameters are checked for consistency, and if the library precursor ion m/z value is distinct from its elucidated counterpart or the isolation widths do not overlap, the spectra should not be considered as a positive match. It is highly recommended to deploy this feature in searching for spectral analogies.

The identified fragment structures can be displayed or can be further processed. The fragment structures may not necessarily reflect directly any specific substructure of the elucidated molecule because the fragment ions are product-ions of complex decomposition reactions. If a non-resonance, simple bond cleavage reaction has taken place, the fragment structure is structurally identical (isomorph) with a part of the primary (parent) structure or substructure. However, if rearrangement, chain shortening, ring closure, contraction or opening, or displacement or resonance reactions are involved, the fragment structure may not exactly match any part of the primary structure. Therefore, it could be beneficial to translate fragment structures to substructures if they are not isomorph. It is a further idea of the invention to transform any identified fragment structure into a substructure that can be topologically matched with the primary structure. This can be accomplished by maintaining a connectivity link between fragment atoms/bonds and atoms/bonds of the primary library structure during manual or automatic fragment structure establishment processes or by atom and/or bond mapping procedures that are able to establish this link. The connectivity link earmarks substructure corresponding to fragment structure of the primary structure. Since the course of the fragmentation and/or rearrangement reactions is often dependent on the structural environment adjacent to atoms and/or bonds involved in decomposition reactions, the substructure corresponding to fragment structure can be enlarged up to atoms/bonds expected to have influence on the overall decomposition process. The obtained substructures can be displayed or further processed.

The collective structural information and/or alternative structural candidates can be reconstructed from the identified fragments structures of substructures and/or additional structural characteristics using a structure generator and/or a structure assembly and/or structure reduction system. The reconstruction approach is based on exhaustive generation of structural isomers considering the structural characteristic that may contain duplicate and/or overlapping information. Such a system computes a complete set of connectivity isomers free from duplicates. The additional structural characteristics serve as selective restriction criteria since the number of generated structural isomers can be immense if no restrictions, or restrictions that are too general, are applied. Substructures identified by means of this invention are the most efficient restriction criteria that reduce the potential structural space to a limited number of structures.

The structural characteristic can comprise exact or integer, average or monoisotopic molecular mass, molecular formula, a priori known functional groups, isotopic pattern, mass defect (which is the difference between the exact mass of an atom, molecule, ion, or radical and its integer mass (Sparkman 2000)), nitrogen rule (which means that an odd-electron ion will be at an even mass number if it contains an even number of nitrogen atoms (McLafferty, 1993)), rings plus double-bonds (which is an expression used to describe a method of determining the number of rings and/or double bonds in a neutral molecule or ion (Sparkman, 2000)), neutral losses (which are neutral species lost in the formation of the fragment ions, especially those formed directly from the molecular or pseudomolecular ion (McLafferty, 1993)), and/or physico-chemical properties of the elucidated structure.

If more than one structure is proposed, they can be ranked according to chemical relevance or can be manually sorted by an operator. Generation of structural candidates can precede calculations of possible, chemically relevant molecular formulas (elemental composition) from integer or exact monoisotopic molecular mass. A list of possible molecular formulas along with other already mentioned supplementary structural characteristics can effectively reduce the number of possible structural arrangements in structure generation process. In addition to determination of the structure of unknowns, the method of the invention can determine which structures or substructures cannot encompass the analyzed molecule.

The performance of the method of the invention can be continuously improved by adding additional structurally characterized product-ion spectra to the library, which can be obtained from molecules previously structurally characterized using this method. If the method unambiguously determines the molecular structure of the elucidated molecule and this compound exhibits product-ion spectra that are not included in the library, their precursor ions can be subsequently structurally characterized as described above. In this way, structurally characterized product-ion spectra can be added to the library to enhance the knowledge base. This "self-improving" feature is also part of the invention.

Exemplary activation and dissociation methods for preparing ion fragments include the following. Collisionally activated dissociation (CAD), also known as collision induced dissociation (CID), is a method by which analyte ions are dissociated by energetic collisions with neutral or charged species, resulting in fragment ions which can be subsequently mass analyzed. Mass analysis of fragment ions from a selected parent ion can provide certain sequence or other structural information relating to the parent ion. Such methods are generally referred to as tandem mass spectrometry methods and are the basis of the some of MS based biomolecular sequencing schemes being employed today.

Typically, tandem mass spectrometry, also termed "multiple-stage" mass spectrometry (MS.sup.n), involves the coupled use of two or more stages of mass analysis where both the separation and detection steps are based on mass spectrometry. The first stage is used to select an ion or component of a sample from which further structural information is to be obtained. This selected ion is then activated and subsequently fragmented by (CID), photodissociation, electron-capture dissociation (ECD), post-source decay (PSD) or other ion activation and dissociation techniques. The second stage of mass analysis is then used to detect and measure the mass or m/z value of the resulting fragments or product ions. The advent of FTICR-MS has made a significant impact on the utility of tandem, MS.sup.n procedures because of the ability of FTICR to select and trap specific ions of interest and its high resolution and sensitivity when detecting fragment ions. Such ion selection followed by fragmentation routines can be performed multiple times so as to essentially completely dissect the molecular structure of a sample. A two-stage tandem MS experiment would be called a MS-MS or MS/MS experiment while an n-stage tandem MS experiment would be referred to as a MS.sup.n experiment. Depending on the complexity of the sample and the level of structural detail desired, MS.sup.n experiments at values of n greater than 2 may be performed.

Ion trap-based mass spectrometers are particularly well suited for such tandem experiments because the dissociation and measurement steps are temporally rather than spatially separated. For example, a common platform on which tandem mass spectrometry is performed is a triple quadrupole mass spectrometer. The first and third quadrupoles serve as mass filters while the second quadrupole serves as a collision cell for CAD. In a trap based mass spectrometer, parent ion selection and dissociation take place in the same part of the vacuum chamber and are effected by control of the radio frequency wavelengths applied to the trapping elements and the collision gas pressure. Hence, while a triple quadrupole mass analyzer is limited to two stages of mass spectrometry (i.e. MS/MS), ion trap-based mass spectrometers can perform MS.sup.n analysis in which the parent ion is isolated, dissociated, mass analyzed and a fragment ion of interest is isolated, further dissociated, and mass analyzed and so on.

The following example is presented to illustrate the advantages of the present invention and to assist one of ordinary skill in making and using the same. This example is not intended in any way otherwise to limit the scope of the disclosure.

FIG. 2 depicts an example of interpretation of mass spectra of Ampicillin utilizing method present in this invention.

Step 1: Tandem product-ion spectra 10 (MS.sup.3) of an elucidated molecule are acquired from two selected precursor ions (m/z 160 and m/z 191).

Step 2: The product-ion spectra of the elucidated molecule are then compared against the library 12 of structurally characterized product-ion spectra. Four product-ion spectra 14 of four different compounds (PHENOXYMETHYL-PENICILLIN, BENZYLPENICILLIN, CEFACLOR, CEPHALEXIN), acquired at various tandem stages (MS.sup2., MS.sup.3, MS.sup.4), are found in the library as being analogous to product-ion spectra of the elucidated molecule. The MS.sup.3 product-ion spectrum of the elucidated molecule with precursor ion m/z 160 is analogous to two library product-ion spectra (the MS.sup2. product-ion spectrum of PHENOXYMETHYLPENICILLIN and the MS.sup.4. product-ion spectrum of BENZYLPENICILLIN), which are associated with identical fragment structures. The MS.sup.3 product-ion spectrum of the elucidated molecule with precursor ion m/z 191 is also analogous to two library product-ion spectra (the MS.sup.3. product-ion spectrum of CEFACLOR and the MS.sup.3. product-ion spectrum of CEPHALEXIN), which are associated with identical fragment structures.

Step 3: Fragment structures (a,b) and (c,d) 16 associated with retrieved library product-ion spectra are then assumed to correspond to product-ion spectra of the elucidated molecule and, therefore, to be structurally related to the elucidated molecule. The fragment structures can be listed or they can continue to be processed further according to the methods of this invention.

Step 4: Fragment structures (a,b) and (c,d) can be translated 18 into substructures using for example the connectivity link between the original structure (for example CEFACLOR) and its corresponding fragment (structure c). The resulting substructures (e) and (f) 20 can be listed or they can continue to be processed further according to the methods of this invention.

Step 5: Substructures (e) and (f) 20 can then be processed by a structure generator 22 to establish a structural proposal. In this example, the structure generator is able to process graphs that are not-connected.

Step 6: The structure generator reconstructs 24 the structural arrangement of the elucidated molecule shown in this example, which turns out to be the well-known antibiotic ampicillin 26.

REFERENCES

Alfassi, Z. B., "On the Comparison of Different Tests for Identification of a Compound from its Mass Spectrum", J. Am. Soc. Spectrom. 2003, 14, 261–264.

Anderson et al., "A New Algorithm for the Evaluation of Shotgun Peptide Sequencing in Proteomics: Support Vector Machine Classification of Peptide MS/MS Spectra and SEQUEST Scores," J. Proteome Res., 2003, 137–146.

Bristow et al., "Reproducible product-ion tandem mass spectra on various liquid chromatography/mass spectrometry instruments for the development of spectral libraries," Rapid Commun. Mass Spectrom., 2004, 18, 1447–1454.

Damen et al., "Siscom—A New Library Search System for Mass Spectra", Anal. Chim. Acta, 1978, 103, 289–302.

Dancik et al., "De novo Peptide Sequencing via Tandem Mass Spectrometry," J. Comput. Biol., 1999, 6, 327–342.

Dheandhanoo, S., "An Experimental Investigation of the Possibility of Developing a Database for Tandem Mass Spectrometry Using XQQ Instruments," Rapid Commun. Mass Spectrom., 1988, 2, 266–267.

Drablos, F., "Classification of Mass Spectra," J. Chemom., 1992, 6, 119–133.

Enke et al., "Artificial Intelligence Software Approaches are Providing New Insights into MS/MS Spectral Feature/ Substructure Relationships," Anal. Chem., 1987, 59, 1363–1371.

Fernandez-de-Cossio et al., "Automated Interpretation of High-Energy Collision-Induced Dissociation Spectra of Singly Protonated Peptides by 'SeqMS', a Software Aid for De Novo Sequencing by Tandem Mass Spectrometry," Rapid Commun. Mass. Spectrom., 1998, 12, 1867–1878.

Horn et al., "Automated Reduction and Interpretation of High Resolution Electrospray Mass Spectra of Large Molecules," J. Am. Soc. Mass Spectrom., 2000, 11, 320–332.

Joseph et al., "Creation and Comparison of MS/MS Spectral Libraries Using Quadrupole Ion Trap and Triple Quadrupole Mass Spectrometers", Rapid Comm. Mass Spec., 2004, 18, 743–759.

Kerber et al., "MOLGEN-MS: Evaluation of Low Resolution Electron Impact Mass Spectra with MS Classification and Exhaustive Structure Generation" Adv. Mass Spec., 2001, 15, 939–940.

Klagkou et al., "Approaches towards the automated interpretation and prediction of electrospray tandem mass spectra of non-peptidic combinatorial compounds", Rapid Comm. Mass Spec., 2003, 17, 1163–1168.

Lebedev et al., "New Computer Aided Methods for Revealing Structural Features of Unknown Compounds Using Low-Resolution Mass Spectra", J. Chem. Inf. Comput. Sci., 1998, 38, 410–419.

Lindsay et al., "Applications of Artificial Intelligence for Organic Chemistry: The DENDRAL Project", McGraw-Hill, New York, 1980.

Lohninger, H., "MSLIB—a versatile tool for handling and interpreting mass spectral data," Trends Anal. Chem., 1994, 13, 415–418.

Martinez, R. I., "Standard Reference Spectra for Tandem Mass Spectrometry Quality Assurance, Performance, Evaluation and Proficiency Testing: Tandem Mass Spectrometers which use RF-only Multiple Collision Cells," Rapid Commun. Mass Spectrom., 1991, 5, 245–248.

Martinez et al., "Instrument-independent Database for Collisionally Activated Dissociation in Radiofrequency-only Quadrupoles. Single-collision versus Multiple-collision Conditions," Rapid Commun. Mass Spectrom., 1989, 3, 427–431.

McLafferty et al., "Interpretation of Mass Spectra," USB Mill Valley, 1993, 37, 97 and 118–120.

McLafferty et al., "Retrieval and Interpretative Computer Programs for Mass Spectrometry", J. Chem. Inf. Comput. Sci. 1985, 25, 245–252.

Mistrik, R, "Xcalibur HighChem: Mass Frontier Software", HighChem/ThermoFinnigan, 2001, Manual, Revision A, 65–92.

Mistrik, R., "Advances in Mass Spectrometry: New concept for interpretation of mass spectra based on combination of fragmentation mechanism database and a computer expert system", CD-ROM Supplement, Elsevier, Amsterdam, 2004, 16, 821.

Mistrik et al., "A New MS$^n$ Database Concept with Sample Library", Proceedings of 51$^n$ ASMS Conference on Mass Spectrom. and Allied Topics, 2003.

Palmer et al., "Optimalization of Automatically Generated Rules for Predicting the Presence and Absence of Substructures from MS and MS/MS Data," Talanta, 1989, 36, 107–116.

Perkins et al., "Probability-based Protein Identification by Searching Sequence Databases Using Mass Spectrometry Data", Electrophoresis, 1999, 20, 3551–3567.

Pittenauer et al., "Evaluation of ESI-MS$^n$ Ion Trap and MALDI-MS$^n$ Ion Trap/Reflectron TOF Mass Spectra (n=1–3) for Incorporation into a Searchable Database", Proceedings of 52$^n$ ASMS Conference on Mass Spectrom. and Allied Topics, 2004.

Sadygov et al., "Code Developments to Improve the Efficiency of Automated MS/MS Spectra Interpretation," J. of Proteome Res., 2002, 1, 211–215.

Sander, P., "Substance Identification of Ion Trap MS/MS Spectra in a MS/MS Library", Proceedings of 47$^n$ ASMS Conference on Mass Spectrom. and Allied Topics, 1999.

Scsibrany et al., "Common structures in groups of compounds exhibiting similar mass spectra," Fresenius J. Anal. Chem., 1992, 344, 220–222.

Shevchenko et al., "Rapid 'De Novo' Peptide sequencing by a Combination of Nanoelectrospray, Isotopic Labeling and a Quadrupole/Time-of-Flight Mass Spectrometer," Rapid Commun. Mass Spectrom., 1997, 11, 1015–1024.

Stein, S. E., "Chemical Substructure Identification by Mass Spectral Library Searching," J. Am. Soc. Spectrom., 1995, 6, 644–655.

Stein et al., "Optimization and Testing of Mass Spectral Library Search Algorithms for Compound Identification", J. Am. Soc. Spectrom. 1994, 5, 859–866.

Varmuza, K., "Chemometrics in Mass Spectrometry," Int. J. Mass Spectrom. Ion Processes, 1992, 118/119, 811–823.

Varmuza et al. "Advances in Mass Spectrometry: Systematic Structure Elucidation of Organic Compounds Based on Mass Spectra Classification and Isomer Generation", Elsevier, Amsterdam, 1998, 611–626.

Sparkman O. D., "Mass Spectrometry Desk Reference", Global View Publishing, Pittsburgh, 2000, 15, 31 and 36.

Wade et al., "Development of Algorithms for Automated Elucidation of Spectral Feature/Substructure Relationships in Tandem Mass Spectrometry," Anal. Chim. Acta, 1988, 215, 169–186.

Wan K. X. et al., "Comparing Similar Spectra: From Similarity Index to Spectral Contrast Angle," J. Am. Soc. Spectrom., 2002, 13, 85–88.

Warr, W. A., "Indirect Database Approaches and Established Systems. Part 2," Analytical Chemistry, 1993, 65, 1087A-1095A.

Warr, W. A., "Library Search and Spectral Data Dollections. Part 1," Analytical Chemistry, 1993, 65, 1045A-1050A.

Yates III et al., "Method to Correlate Tandem Mass Spectra of Modified Peptides to Amino Acid Sequences in the Database," Anal. Chem., 1995, 67, 1426–1436.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. A method for determining the structure of a molecule, said method comprising the steps of:
    choosing a molecule whose structure is to be determined;
    carrying out tandem mass spectrometry on said molecule to generate product-ion spectra of precursor ions of said molecule;
    comparing said product-ion spectra for said molecule to structurally characterized product-ion spectra to identify chemical structures corresponding to structurally equivalent precursor ions having said structurally characterized product-ion spectra; and
    translating the structural arrangements of structurally equivalent precursor ions identified by said method into substructures of said molecule.

2. The method of claim 1, wherein said molecule comprises a structurally definable chemical entity.

3. The method of claim 1, wherein said molecule comprises a polymer chemical entity of definable or undefinable size.

4. The method of claim 1, wherein said molecule comprises a neutral entity.

5. The method of claim 1, wherein said molecule comprises a charged entity.

6. The method of claim 1, wherein said step of carrying out tandem mass spectrometry comprises employing one or more techniques selected from the group consisting of ion formation, ion selection, ion isolation, ion activation, ion separation and ion detection techniques.

7. The method of claim 1, wherein the structural arrangements of structurally equivalent precursor ions identified by said method are stored in a medium or are listed in readable form.

8. The method of claim 1, wherein the structural arrangements of structurally equivalent precursor ions identified by said method are processed by a structure generator or a structure assembly or a structure reduction system to reconstruct partially or comprehensively the structural arrangement of said molecule whose structure is to be determined.

9. The method of claim 1, wherein, in said comparing step, said product-ion spectra for said molecule are compared to a library of structurally characterized product-ion spectra to identify chemical structures corresponding to structurally equivalent precursor ions from said library.

10. A library of structurally characterized product-ion spectra for identifying precursor ion structures or substructures or charged molecular species, said library comprising:
    a storage medium comprising a plurality of separately acquired product-ion spectra from a plurality of tandem stages from tandem mass spectrometry, wherein said product-ion spectra result from decomposition of precursor ions and include m/z values and the structural arrangement of the precursor ions and/or isolation width, and wherein, further, additional information useful for the identification of structural arrangements or substructures or any other charged molecular species are stored along with said product-ion spectra.

11. The library of claim 10, wherein a plurality of structural arrangements of a given precursor ion can be stored.

12. The library of claim 10, wherein product-ion spectra of singly or multiply charged precursor ions can be stored.

13. The library of claim 10, wherein experimental data or sample preparation information or an acquisition protocol can be stored along with said product-ion spectra.

14. The library of claim 10, wherein primary structural arrangement information for an elucidated molecule prior to decomposition in said mass spectrometer can be stored along with said product-ion spectra.

15. The method of claim 9, wherein said library of structurally characterized product-ion spectra is the library of claim 10.

* * * * *